US012616379B2

(12) United States Patent
Liaqat et al.

(10) Patent No.: US 12,616,379 B2
(45) Date of Patent: May 5, 2026

(54) SYSTEM AND METHOD FOR FILTERING TIME-VARYING DATA FOR PHYSIOLOGICAL SIGNAL PREDICTION

(71) Applicants: THE GOVERNING COUNCIL OF THE UNIVERSITY OF TORONTO, Toronto (CA); UNIVERSITY HEALTH NETWORK, Toronto (CA)

(72) Inventors: Daniyal Liaqat, Toronto (CA); Mohamed Abdalla, Toronto (CA); Eyal De Lara, Toronto (CA); Frank Rudzicz, Toronto (CA); Andrea Gershon, Toronto (CA); Robert Wu, Toronto (CA)

(73) Assignees: THE GOVERNING COUNCIL OF THE UNIVERSITY OF TORONTO, Toronto (CA); UNIVERSITY HEALTH NETWORK, Toronto (CA)

( * ) Notice: Subject to any disclaimer, the term of this patent is extended or adjusted under 35 U.S.C. 154(b) by 846 days.

(21) Appl. No.: 17/456,001

(22) PCT Filed: May 27, 2020

(86) PCT No.: PCT/CA2020/050718
§ 371 (c)(1),
(2) Date: Nov. 22, 2021

(87) PCT Pub. No.: WO2020/237371
PCT Pub. Date: Dec. 3, 2020

(65) Prior Publication Data
US 2023/0263400 A1     Aug. 24, 2023

Related U.S. Application Data

(60) Provisional application No. 62/855,258, filed on May 31, 2019.

(30) Foreign Application Priority Data

Sep. 12, 2019     (GB) ..................................... 1913131

(51) Int. Cl.
*A61B 5/02* (2006.01)
*A61B 5/00* (2006.01)

(52) U.S. Cl.
CPC .............. *A61B 5/02* (2013.01); *A61B 5/7275* (2013.01)

(58) Field of Classification Search
CPC ......... A61B 5/02; A61B 5/0816; A61B 5/113; A61B 5/1135; A61B 5/681; A61B 5/7214;
(Continued)

(56) References Cited

U.S. PATENT DOCUMENTS

2003/0153821 A1     8/2003     Berner et al.
2013/0103624 A1     4/2013     Thieberger
(Continued)

FOREIGN PATENT DOCUMENTS

CN          106251583 A          12/2016
CN          106264499 A          1/2017
(Continued)

OTHER PUBLICATIONS

Extended European Search Report for European application No. 20813874.3, EPO, dated: May 22, 2023.
(Continued)

*Primary Examiner* — George Manuel
(74) *Attorney, Agent, or Firm* — Marc Lampert; Bhole IP Law

(57) ABSTRACT

Systems and methods for filtering time-varying data for filtering and extracting a predicted physiological signal. A method including: segmenting the time-varying data into
(Continued)

temporal windows; using a trained filter machine learning model, predicting an error for each prediction of the physiological signal for each window of time-varying data, the filter machine learning model trained using physiological signal predictions based on training time-varying data and known values of the physiological signal for the training time-varying data; discarding each window of time-varying data when the predicted error for such window is greater than a threshold; and where the window of time-varying data is not discarded, outputting at least one of the window of time-varying data and the predicted error for each prediction of the physiological signal.

18 Claims, 9 Drawing Sheets

(58) Field of Classification Search
CPC ..... A61B 5/725; A61B 5/7267; A61B 5/7275; G06N 20/10; G06N 20/20; G06N 3/044; G06N 3/045; G06N 3/048; G06N 3/08; G06N 5/01; G16H 50/20; G16H 50/30
See application file for complete search history.

(56) References Cited

U.S. PATENT DOCUMENTS

| | | |
|---|---|---|
| 2013/0345585 A1 | 12/2013 | Gopal Samy et al. |
| 2017/0076217 A1* | 3/2017 | Krumm ................. G06N 20/00 |
| 2017/0185733 A1* | 6/2017 | Nogueira ............ A61B 5/1495 |
| 2018/0233227 A1 | 8/2018 | Galloway et al. |
| 2018/0350468 A1 | 12/2018 | Friedman et al. |
| 2019/0110755 A1 | 4/2019 | Capodilupo et al. |

FOREIGN PATENT DOCUMENTS

| | | |
|---|---|---|
| CN | 107530003 A | 1/2018 |
| WO | 2016077786 A1 | 5/2016 |

OTHER PUBLICATIONS

PCT International Preliminary Report on Patentability for International Patent Application No. PCT/CA2020/050718 Issued Nov. 16, 2021.
PCT International Search Report for International Patent Application No. PCT/CA2020/050718 issued Aug. 24, 2020.
Combined Search and Examination Report for GB1913131.7, UK Intellectual Property Office, dated: Mar. 13, 2020.

* cited by examiner

300

Receive time-
varying data
302

Segment into
windows
304

Predict error for
each window
306

Discard if above
threshold
308

Perform desired
prediction
310

Output desired
prediction
312

SYSTEM AND METHOD FOR FILTERING TIME-VARYING DATA FOR PHYSIOLOGICAL SIGNAL PREDICTION

TECHNICAL FIELD

The following relates generally to real-time data processing; and more specifically, to a system and method for filtering time-varying data for physiological signal prediction.

BACKGROUND

Receiving and processing physiological signals in real-time can provide an important window into the health and well-being of an individual. For example, respiratory rate is a vital physiological signal that may be useful for a multitude of clinical applications, especially if measured outside of controlled clinical settings (referred to as "in-the-wild"). Some approaches to in-the-wild physiological signal monitoring can require specialized, expensive, invasive, and/or cumbersome devices or procedures. In addition, some approaches may be overly susceptible to noise in the readings, such that meaningful signals received in-the-wild may not be practical or useful due to insufficient accuracy or computational burden.

SUMMARY

In an aspect, there is provided a computer-implemented method for filtering time-varying data for physiological signal prediction, the physiological signal predicted based on the time-varying data, the method comprising: receiving the time-varying data; segmenting the time-varying data into temporal windows; using a trained filter machine learning model, predicting an error for each prediction of the physiological signal for each window of time-varying data, the filter machine learning model trained using physiological signal predictions based on training time-varying data and known values of the physiological signal for the training time-varying data; discarding each window of time-varying data when the predicted error for such window is greater than a threshold; and where the window of time-varying data is not discarded, outputting at least one of the window of time-varying data and the predicted error for each prediction of the physiological signal.

In a particular case of the method, the threshold is tunable by a user.

In another case, input to the filter machine learning model comprises one or more aggregate measures of the time-varying data.

In yet another case, the physiological signal prediction comprises using an extraction machine learning model to predict the physiological signal using the time-varying data as input, the extraction machine learning model trained using the training time-varying data and known values of the physiological signal for the training time-varying data.

In yet another case, training of the filter machine learning model comprises performing principal component analysis (PCA) on the predictions of the extraction machine learning model and passing the PCA output to the filter machine learning model for training.

In yet another case, the portion of training time-varying data used to train the extraction machine learning model is different than the portion of training time-varying data used to make predictions by the extraction machine learning model for training of the filter machine learning model.

In yet another case, the physiological signal comprises respiratory rate and the time-varying data comprises continuous motion sensor data from one or more movement sensors.

In yet another case, the continuous motion sensor data is received from at least one of an accelerometer, a magnetometer, and a gyroscope.

In yet another case, input to the filter machine learning model comprises a plurality of aggregate measures for each axis of the continuous motion sensor data.

In yet another case, an Inertial Measurement Unit (IMU) in a smartwatch comprises at least one of the accelerometer, the magnetometer, and the gyroscope.

In another aspect, there is provided a system for filtering time-varying data for physiological signal prediction, the physiological signal predicted based on the time-varying data, the system comprising one or more processors and a data storage, the one or more processors in communication with the data storage device and configured to execute: an interface module to receive the time-varying data and segment the time-varying data into temporal windows; and a filter module to: using a trained filter machine learning model, predict an error for each prediction of the physiological signal by the trained extraction machine learning model for each window of time-varying data, the filter machine learning model trained using physiological signal predictions based on training time-varying data and known values of the physiological signal for the training time-varying data; discard the window of time-varying data when the predicted error for such window is greater than a threshold; and where the window of time-varying data is not discarded, output at least one of the window of time-varying data and the predicted error for each prediction of the physiological signal.

In a particular case of the system, the threshold is tunable by a user via input to the interface module.

In another case, input to the filter machine learning model comprises one or more aggregate measures of the time-varying data.

In yet another case, the physiological signal prediction comprises using an extraction machine learning model to predict the physiological signal using the time-varying data as input, the extraction machine learning model trained using the training time-varying data and known values of the physiological signal for the training time-varying data.

In yet another case, training of the filter machine learning model comprises performing principal component analysis (PCA) on the predictions of the extraction machine learning model and passing the PCA output to the filter machine learning model for training.

In yet another case, the portion of training time-varying data used to train the extraction machine learning model is different than the portion of training time-varying data used to make predictions by the extraction machine learning model for training of the filter machine learning model.

In yet another case, the physiological signal comprises respiratory rate and the time-varying data comprises continuous motion sensor data from one or more movement sensors.

In yet another case, the continuous motion sensor data is received from at least one of an accelerometer, a magnetometer, and a gyroscope.

In yet another case, input to the filter machine learning model comprises a plurality of aggregate measures for each axis of the continuous motion sensor data.

In yet another case, an Inertial Measurement Unit (IMU) in a smartwatch comprises at least one of the accelerometer, the magnetometer, and the gyroscope.

In another aspect, there is provided a computer-implemented method for extracting a physiological signal from time-varying data, the method comprising: receiving the time-varying data; segmenting the time-varying data into temporal windows; extracting a physiological signal for each temporal window using a Convolutional Neural Network (CNN), input to the CNN comprising the segmented time-varying data, the CNN trained using training time-varying data and known values of the physiological signal for the training time-varying data; and outputting the extracted physiological signal.

In another aspect, there is provided a system for extracting a physiological signal from time-varying data, the system comprising one or more processors and a data storage, the one or more processors in communication with the data storage device and configured to execute: an interface module to receive the time-varying data and segment the time-varying data into temporal windows; and an extractor module to extract a physiological signal for each temporal window using a Convolutional Neural Network (CNN), input to the CNN comprising the segmented time-varying data, the CNN trained using training time-varying data and known values of the physiological signal for the training time-varying data, the interface module outputting the extracted physiological signal.

In another aspect, there is provided a computer-implemented method for training two interoperable machine learning models using time-varying training data, an extraction machine learning model predicting an outcome on the time-varying data and a filter machine learning model predicting an error of the outcome prediction of the extraction machine learning model, the time-varying training data comprising time-varying data with known outcomes, the method comprising: training the extraction machine learning model comprising passing a majority portion of the training time-varying data through the extraction machine learning model with the known outcomes as labels for training; and training the filter machine learning model comprising: passing a minority portion of the training time-varying data through the extraction machine learning model to output predicted outcomes; determining an error for each predicted outcome compared to the known outcome; and passing the minority portion of the training time-varying data through the filter machine learning model with the determined errors as labels for training.

In a particular case of the method, the time-varying training data comprises time-varying data from a plurality of sources, and wherein the division of majority portion and minority portion applies to the time-varying training data from each of the plurality of sources.

In another case, a portion of the training time-varying data that is separate from the majority portion and the minority portion is used for testing both the filter machine learning model and the extraction machine learning model.

These and other aspects are contemplated and described herein. It will be appreciated that the foregoing summary sets out representative aspects of systems and methods to assist skilled readers in understanding the following detailed description.

BRIEF DESCRIPTION OF THE DRAWINGS

The features of the invention will become more apparent in the following detailed description in which reference is made to the appended drawings wherein.

DETAILED DESCRIPTION

Figure 1:
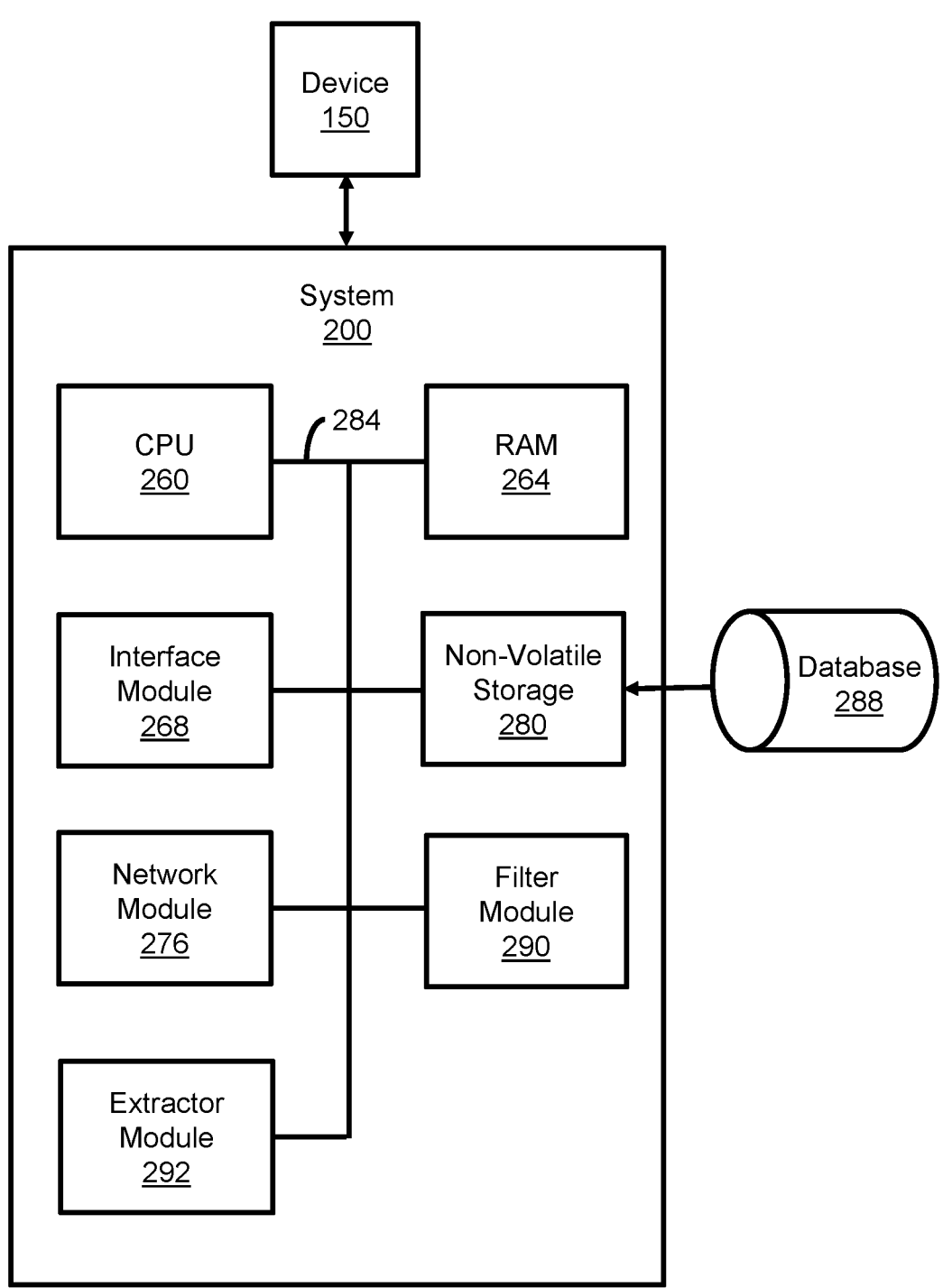
FIG. 1 is schematic diagram of a system for filtering time-varying data for predictive analysis, and for physiological signal prediction, according to an embodiment.

Embodiments will now be described with reference to the figures. For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

The following relates generally to real-time data processing; and more specifically, to a system and method for filtering time-varying data for physiological signal prediction.

Continuous monitoring of physiological signals is an important objective for personalized health care. For example, respiratory rate is one such signal that is useful for a multitude of clinical applications. Higher respiratory rates are a strong predictor of cardiac arrest and have been linked to negative outcomes in hospital wards and emergency rooms. For example, a respiratory rate over 27 breaths/minute was a significant predictor of cardiac arrest. As an early warning measure for cardiac arrest, respiratory rates were scored by a study between 9 and 30 in increments of 5 (e.g. 9-14 or 15-20), and it was reported that 21% of ward patients with a respiratory rate between 25 and 29 died in hospital. Studies recommend that patients with a respiratory rate greater than 24 breaths/minute should be monitored closely and those with respiratory rate greater than 27 should receive immediate medical attention. Continuous monitoring of respiratory rate could lead to diagnoses and treatments for respiratory conditions such as asthma and chronic obstructive pulmonary disease (COPD), and also non-respiratory conditions such as cardiac arrest, heart failure, panic attacks and anxiety disorders; all of which have shortness of breath as a potential symptom.

Some approaches to measuring physiological signals, such as respiratory rate, require using dedicated devices, such as chest band sensors. However, these devices are generally specialized, expensive and cumbersome to wear on a daily basis, and the effort of having to use an extra device will dissuade all but the most determined users. Some approaches attempt to use generalized wearable devices, such as a smartwatch, based on accelerometer, magnetometer, and gyroscope data. However, such approaches have generally been unreliable and inaccurate in the presence of motion and only have a measure of accuracy in controlled or low-motion settings. Accordingly, determining real-time physiological signals in-the-wild is a substantial technological challenge.

Advantageously, the present embodiments can allow for almost effortless physiological signal processing using generally inexpensive devices that are readily available and easy to use. For example, in the present embodiments, smartwatches can be used for respiratory rate monitoring. Smartwatches can be relatively inexpensive off-the-shelf devices that contain an assortment of sensors. They can serve multiple purposes, making them more appealing for users to wear day-after-day.

In some approaches, smartwatches can be used for respiratory rate monitoring by making use of accelerometer, magnetometer, and/or gyroscope sensors. Breathing produces subtle, periodic motions that can be measured by an Inertial Measurement Unit (IMU) in the smartwatch. These approaches generally use the periodic nature of breathing to detect a signal that falls within some frequency that corresponds to the expected breathing rate (for example, 9-30 breaths/min). However, such approaches are generally highly susceptible to motion artifacts. Accordingly, such approaches are generally confined to conduct measurements in controlled or low-motion settings. In contrast, advantageously, the present embodiments can generally perform continuous respiratory rate monitoring in everyday environments and during daily tasks.

While some of the present embodiments refer to measurements of periodic movement to determine a respiratory rate as the extracted physiological signal, it is understood that the present embodiments can be used to extract any suitable physiological signal; for example, respiratory rate, heart rate, blood flow, muscle current, skin conductance, neurological electrical activity, or the like. Additionally, while some of the present embodiments refer to smartwatches with accelerometers, magnetometers, and gyroscopes as the sensors, and a chest band as a ground-truth device, it is understood that the present embodiments can be used to with any suitable device and sensors; for example, a smartphone, a photoplethysmogram (PPG), a pulse oximeter, a camera, an electrode bank, a device specialized for the methods described herein, or the like.

FIG. 1 illustrates a schematic diagram of a system 200 for filtering time-varying data for predictive analysis, and for physiological signal prediction, according to an embodiment. As shown, the system 200 has a number of physical and logical components, including a central processing unit ("CPU") 260, random access memory ("RAM") 264, an interface module 268, a network module 276, non-volatile storage 280, and a local bus 284 enabling CPU 260 to communicate with the other components. CPU 260 can include one or more processors. RAM 264 provides relatively responsive volatile storage to CPU 260. In some cases, the system 200 can be in communication with a device, for example a wearable device such as a smartwatch, via, for example, the interface module 268. The interface module 268 enables input to be provided; for example, directly via a user input device, or indirectly, for example via the device 150. The interface module 268 also enables output to be provided; for example, directly via a user display, or indirectly, for example via the device 150. The network module 276 permits communication with other systems or computing devices; for example, over a local area network or over the Internet. Non-volatile storage 280 can store an operating system and programs, including computer-executable instructions for implementing the methods described herein, as well as any derivative or related data. In some cases, this data can be stored in a database 288. During operation of the system 200, the operating system, the programs and the data may be retrieved from the non-volatile storage 280 and placed in RAM 264 to facilitate execution. In other embodiments, any operating system, programs, or instructions can be executed in hardware, specialized microprocessors, logic arrays, or the like.

In an embodiment, the CPU 260 can be configured to execute a filter module 290 and an extractor module 292. In some cases, the interface module 268 and/or the network module 276 can be also executed on the CPU 260.

The system 200 can be used for physiological signal prediction; for example, for respiratory rate monitoring. In an embodiment, the system 200 can use a filter machine learning model, such as a Random Forest (RF) model, to act as a filter and reject physiological signals received from one or more sensors that can result in an inaccurate reading. Sensor readings that pass the filter can be fed into an extraction machine learning model, for example a Convolutional Neural Network (CNN) model, to extract the physiological signal from the sensor data; for example, extracting a respiratory rate from accelerometer, magnetometer, and gyroscope data on a smartwatch. Other approaches to physiological signal filters are generally inflexible; for example, they assume that excessive motion is the sole cause for inaccurate respiratory rate readings, and reject readings if the level of motion surpasses some threshold. In this way, other approaches only filter the source signal based on the amount of noise present. Advantageously, the present embodiments do not make any explicit assumptions about what causes unreliable readings and instead learn what causes an extractor in the extraction machine learning model to be inaccurate. The present embodiments can take into account both the original signal and its interaction with the extraction of the physiological signal.

Generally, a technical problem in the art is that not all data from sensors, such as an accelerometer, magnetometer, and gyroscope on a smartwatch, will result in a reliable signal reading. Advantageously, the present embodiments can identify when the signal reading is reliable though the use of the filter module 290 and the extractor module 292. The extractor module 292 can be used to take sensor data as input and produce an estimated physiological signal. The filter module 290 can be used to take the sensor data as input, but instead of predicting the physiological signal, it can predict an error that the extractor module 292 will have on this input. To determine if a reliable physiological signal is produced, the predicted error from the filter module 290 can be compared to a threshold, for example, a threshold defined by the user. If the predicted error is below the threshold, the sensor data is passed to the extractor module 292 which can produce the estimated physiological signal.

Figure 2:
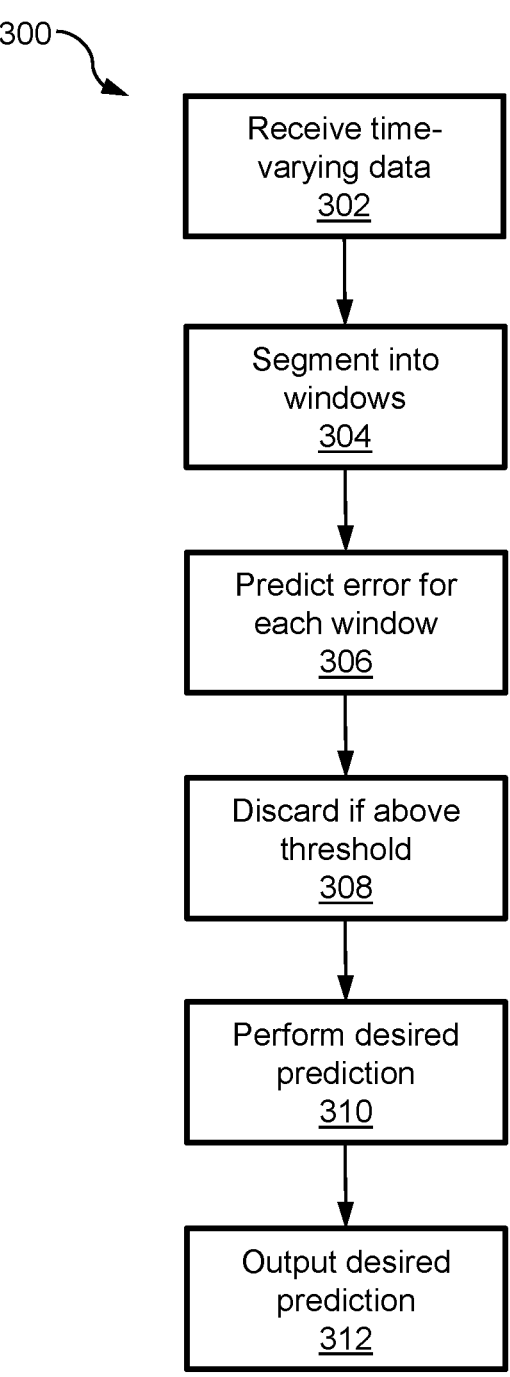
FIG. 2 is a flowchart for a method for filtering time-varying data for predictive analysis, and for physiological signal prediction, according to an embodiment.

Turning to FIG. 2, a method for filtering time-varying data for predictive analysis 300, according to an embodiment, is shown. In a particular case, the time-varying data can be a continuous signal, for example, a continuous data stream received from a measurement sensor. Continuous is understood to also include regular, periodic receptions of data. At block 302, the interface module 268 receives the time-varying data; for example, sensor data from one or more sensors of the device 150. The time-varying data is at least partially-correlated with a desired aspect to be predicted; for example, the sensor data is at least partially correlated with a physiological signal. In some cases, the interface module 268 can receive the time-varying data in real-time or approximately real-time, and in other cases, it can receive it after the time-varying data has already been collected. In some cases, the system 200 can be a separate device than the computing device that collected the time-varying data.

At block 304, the interface module 268 segments the time-varying data into successive temporal windows.

At block 306, the filter module 290 uses a trained filter machine learning model to predict error for each window if the window were to be processed by a trained extraction machine learning model of the extractor module 292. For example, predicting the error of a prediction of the physiological signal by the extractor module 292. At block 308, the filter module 290 discards the time-varying data in each window if the predicted error for such window is greater than a threshold. The threshold can be tunable by a user or administrator, or in other cases, can be fixed.

At block 310, if a given window is not discarded, the time-varying data of such window is passed to the extractor module 292 for performance of the prediction of the aspect. The extractor module 292 performs the prediction based on each window of the time-varying data using the trained extraction machine learning model. In an example, the desired aspect to be predicted can be a physiological signal based on the sensor data; for example, respiratory rate.

At block 312, the interface module 268 outputs the prediction.

The extraction machine learning model can be trained by the extractor module 292 using, for example, a training dataset with ground-truth labelling. For example, sensor data with known values of the physiological signal; for example, gyroscope, magnetometer, and accelerometer smartwatch sensor data with ground-truth values of respiratory rate acquired from a chest band. The filter machine learning model can be trained by the filter module 290 using error of the predictions of the extraction machine learning model on the training dataset and the time-varying data. The error of the predictions of the extraction machine learning model can be determined by comparing the predictions of the extraction machine learning model with associated ground-truth values. For example, the filter machine learning model can be trained using the sensor data (for example, the gyroscope, magnetometer, and accelerometer smartwatch sensor data) and the error of the physiological signal (for example, respiratory rate) predictions of the extraction machine learning model. The system 200 advantageously predicts error to ultimately provide substantially improved accuracy and computing efficiency (as evidenced in the example experiments described herein), rather than relying on error determined after-the-fact for comparison to a threshold or relying on a selection scheme to pre-filter data.

Advantageously, the system 200 can only require that the filter module 290 be run on each window of time-varying data, while the extractor module 292 then only has to run on windows where the predicted error was below a threshold. This means that the extractor module 292, which is generally a much more complicated model, runs much less frequently. In some cases, this allows the system 200 to be run in real-time and for longer periods on battery-powered and processing-constrained devices like a smartwatch or smartphone.

Figure 3:
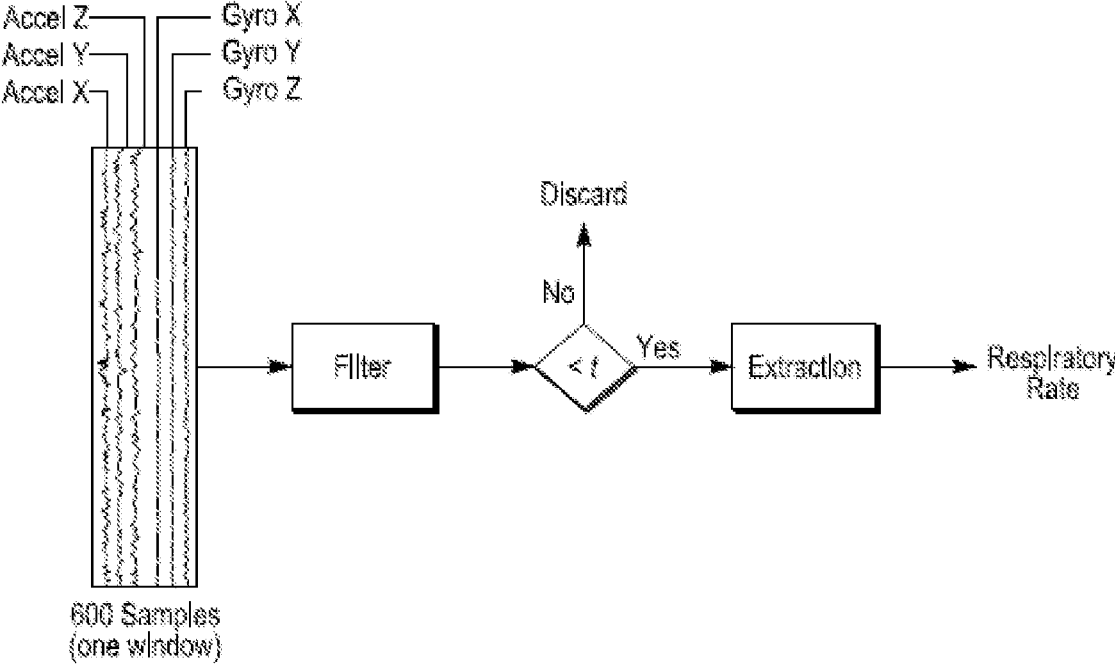
FIG. 3 is an example diagram of the system of FIG. 1 as applied to an example extraction of a respiratory rate from a smartwatch.

FIG. 3 illustrates an example diagram of the system 200 as applied to an example extraction of a respiratory rate from a smartwatch. In this case, the sensors providing the input data are a 3-dimensional accelerometer and a 3-dimensional gyroscope. The input data comprising 600 samples is inputted to the filter module 290, which decides whether to discard the data due to error. If the data is not discarded, the extractor module 292 determines the respiratory rate. Although, during operation, the system 200 can apply the filter module 290 before the extractor module 292, in some cases during development and training, the extraction machine learning model of the extractor module 292 can be trained before the filter machine learning model of the filter module 290.

In an embodiment, the extractor module 292 can extract the physiological signal using a Convolutional Neural Network (CNN) as the extraction machine learning model. In this embodiment, a CNN model is employed to extract the physiological signal because CNN models generally excel at detecting patterns in spatial or temporal sequences of multi-channel data and time series data. In further embodiments, other machine learning models can be used; for example, a recurrent neural network (RNN) such as a long short-term memory (LSTM) model. The present inventors have determined that for the present system 200, CNN models generally outperform LSTMs and are generally less computationally expensive; which can be important for a model designed to run on a resource constrained device such as a smartwatch.

In the present embodiments, the extraction machine learning model is used to extract the physiological signal, using the fact that such a signal has a distinct pattern. The signal is extracted in time series data, where data from each sensor can be represented by one or more channels. For example, to extract a respiratory signal, accelerometer, magnetometer, and gyroscope sensor data, as measured by an Inertial Measurement Unit (IMU) in a smartwatch, is received as input data, where the axes of the accelerometer, magnetometer, and gyroscope are represented as channels.

Figure 4:
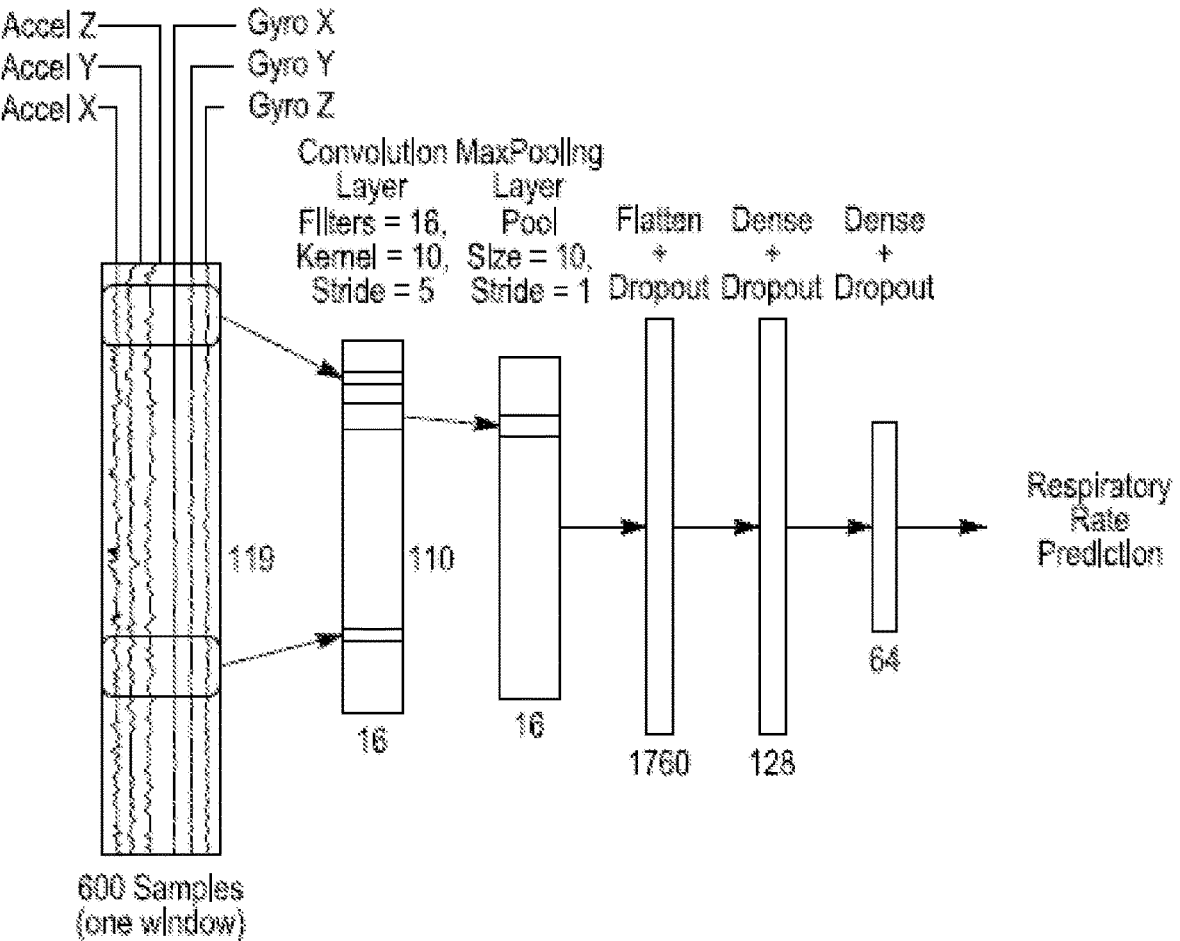
FIG. 4 is an example diagrammatic illustration of an extraction machine learning model according to the embodiment of FIG. 1.

An example architecture for the extraction machine learning model is diagrammatically illustrated in FIG. 4. In this example, the extraction machine learning model is a CNN. The present inventors advantageously determined that a five-layer CNN, as exemplified in FIG. 4 and described herein, provides exceptional accuracy, while not being computationally resource intensive; such that, the CNN of the present embodiments can be implemented on a lower-power, low-resources device such as a smartwatch. In this example, the CNN receives 30 second windows of 6 axes of raw accelerometer and gyroscope data (representing 600 samples). While this example uses a 30 second window and 6 axes of input data, it is understood that any suitable window size and number of input channels can be used. In this example, it was determined by the present inventors that a 30 second window size produced sufficient results. In further cases, the raw data can be processed prior to being used by the extraction machine learning model; for example, performing a Fourier transform or taking a derivative of each axis. However, the present inventors determined that using raw data generally performed better. In this example, a shallow CNN is used comprising a single convolutional layer with a rectified linear unit activation, 16 hidden units, a kernel size of 5 and stride size of 1. Following the convolutional layer, a max pooling layer is used with a pool-size of 10 and stride of 1. The output of the pooling layer is connected to a dense layer with 128 hidden units that feed into another dense layer with 64 hidden units. Both dense layers use a rectified linear activation and a 0.2 dropout after each. The second dense layer connects to a single predictive node, again with a rectified linear activation. While the architecture of the present example was determined by the present inventors to provide a sufficient extraction of the output signal, it is understood that any suitable architecture can be used.

In some cases, the extraction machine learning model can be optimized; for example, using adaptive moment estimation, with mean absolute error as the loss function. In some cases, the extraction machine learning model can be implemented using a Keras framework, and for any unspecified hyper-parameters, the Keras default values can be used.

The extraction machine learning model can be trained by the extractor module 292 to predict the physiological signal using labelled examples of the physiological signal. For example, for respiratory rate signals, respiratory rate labels can be obtained from a chest band, as described herein. In further cases, the extractor module 292 can train the extraction machine learning model using unlabelled or partially-labelled physiological signal data by first using, for example, a clustering technique.

In an embodiment, the filter module 290 can filter the physiological signal by predicting the error in the extractor module 292 using the filter machine learning model. Some other approaches operate on the idea that respiratory rate extraction is generally inaccurate in the presence of motion. Therefore, such approaches employ simple filters that assume the amount of motion is directly related to the error. An example of such a filter is one that looks at the average vector magnitude of the x, y and z axes of the previous n accelerometer readings:

$$\text{accept (window)} = \frac{\sum_{i=1}^{n} \sqrt{x_i^2 + y_i^2 + z_i^2}}{n} < t$$

In example experiments conducted by the present inventors, a window size of 30 seconds and sampling rate of 20 were used; which means that n=600. So for a given window of 600 samples, if the value resulting from the above equation exceeds some predetermined threshold t, then this window will not be passed on for extraction of the signal. As described herein, such simple filters generally do not perform well and are generally not intuitive.

In an embodiment, the filter module 290 can filter the physiological signal using a random forest regression-based model as the filter machine learning model. Instead of assuming that motion is the only source of error and explicitly using a formula to estimate the amount of motion, the filter module 290 trains a classifier (the filter machine learning model) to learn what causes errors; particularly, it learns the interaction between the input data and the extractor module 292. In further embodiments, other machine learning techniques can be used as the filter machine learning model; for example, a Naive Bayes classifier, a support vector machine, a k-nearest neighbour, or the like. The present inventors have determined that for the present system 200, the random forest regression-based model generally outperforms other approaches when considering computational efficiency. Unlike the simple filter described above, which estimates the amount of motion in a window, the filter module 290 predicts the error that can be expected if the extractor module 292 were to be applied on a given window. Advantageously, the present inventors determined that the filter module 290 produces a filter that is relatively easier to tune since the threshold directly controls error in the extracted physiological signal; which users care about and understand, rather than the motion within a window, which is considerably harder to understand.

In some cases, the filter module 290 can take as input a summary of the sensor data. In an example, the filter module 290 feeds as input to the random forest model a summary of accelerometer, magnetometer, and gyroscope data from a smartwatch. The summary can be obtained by determining a plurality of aggregate measures; for example, 16 aggregate measures for each axis. In this example, the measures are the mean, median, minimum, maximum, kurtosis, skew and $10^{th}$, $20^{th}$, . . . , $90^{th}$ percentiles. Advantageously, in an example, this summary can reduce the dimension of each window from 6 vectors of length 600 to 6 vectors of length 26. The resulting 6 vectors can then be concatenated into a single vector; in this example, a vector of length 96. In some cases, principal component analysis (PCA) can be used to further reduce the vector's dimension; for example, to an empirically determined length of 20. The output of PCA can then be used as input to the filter machine learning model. Generally, a PCA projection matrix is determined using training data only.

For labels on the input data to the filter machine learning model, the filter module 290 uses error of the extractor module 292. For example, for each input signal, the extractor module predicts the physiological signal using the trained extraction machine learning model and the filter module 290 determines an absolute difference between the predicted physiological signal and a ground truth physiological signal as the error. The filter module 290 can thus use the filter machine learning model to predict such error. The ground truth signal being, for example, the labelled examples of the physiological signal described herein.

In some cases, the filter machine learning model and the extraction machine learning model (collectively, the "Models") can use both training and testing. In some cases, the data used to train the Models can be obtained from multiple participants. In some cases, to prevent over-fitting and ensure that the results are generalizable, the Models can be validated using validation techniques; for example, a leave-one-out cross validation scheme. For example, for a particular participant x (for example, a new participant), the Models can be trained using data from other participants (for example, all previous participants) except for the particular participant x. In this way, when the trained Models are evaluated on a particular participant, the Models have never seen data from that participant during training. It also means that the results used to train the Models present are averages across participants.

Figure 5:
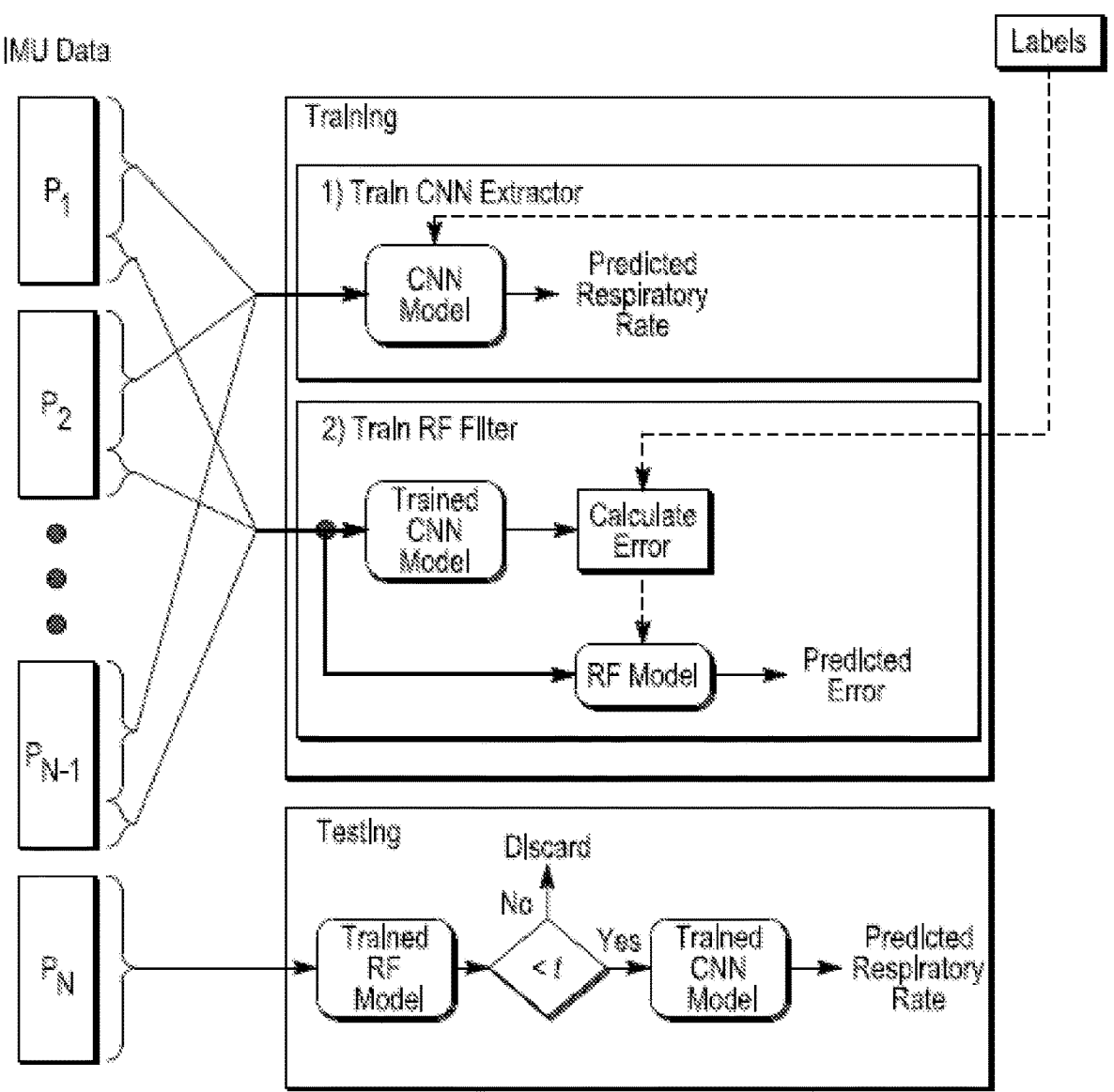
FIG. 5 is an example diagrammatic illustration of the system of FIG. 1 for the prediction of respiratory rate.

In some cases, caution may need to be heeded with respect to training the filter machine learning model because its labels are generally dependent on the output of the extraction machine learning model, which could potentially bias the filter machine learning model. For example, if a window that is used to train the filter machine learning model was previously used to train the extraction machine learning model, it would be expected that the extraction machine learning model is more accurate in extracting respiratory rate from this window. Therefore, the error that the filter machine learning model is attempting to predict may not be a true representation of the error that would be expected if the extraction machine learning model was predicting on unseen data. In some cases, to address such problem, a minority portion (<50%) of hold out data (for example, 10%) is held out from each source (in this case, participant) in the training data of the extraction machine learning model. This smaller amount of hold out data is not used to train the extraction machine learning model. Once the extraction machine learning model has been trained, the hold out data is passed through the extraction machine learning model and the extractor module 292 predicts the physiological signal. The filter module 290 can determine an absolute error for these predictions and use these errors as labels to train the first machine leaning model (acting as the filter). An example implementation of such a scheme is diagrammatically illustrated in FIG. 5, for the example of determining a respiratory rate for the $N^{th}$ participant ($P_N$) using IMU training data from N−1 previous participants ($P_1$ . . . $P_{N-1}$).

The present inventors validated the present embodiments using example experiments comprising determining a respiratory rate from smartwatch sensors in the wild. In the example experiments, a dataset was collected that contained data from a smartwatch and a ground truth device. The dataset contained data from 14 participants, 7 of which were healthy and 7 had chronic lung disease (3 female and 4 male in both groups, healthy group mean age: 28.4 years, chronic lung disease group mean age: 69.3 years). There is a significant age difference in these groups because COPD occurs most commonly in older adults. All participants were asked to wear a smartwatch, an LG Urbane, on their non-dominant hand to collect accelerometer and gyroscope data. Data from both the accelerometer and gyroscope were recorded at 20 Hz because generally this is a sufficient sampling frequency to capture the respiratory rate signal which generally has a frequency between 0.13 and 0.66. For the purposes of these example experiments, the collected data was communicated to a server where the Models were trained. As shown as part of the example experiments, the system 200, including the Models, can be deployed on the smartwatch itself to determine respiratory rate.

In the example experiments, to obtain ground truth data, participants also wore a chest band, a Zephyr BioHarness 3.0, which uses a capacitive pressure sensor to measure expansion and contraction of the chest. For each respiratory rate reading from the chest band, the preceding 30 seconds of accelerometer and gyroscope data was considered as a window. The participants were asked to complete specific activities in a lab while wearing both the smartwatch and chest band. This training data set can be considered semi-controlled because, while participants were asked to perform specific activities, there were no restrictions on how to perform the activities. For example, participants were not told how to place or move their arms and had the freedom to move their arms however they wanted during the example experiments. The activities performed during the semi-controlled training portion, listed in the summary of TABLE 1, were selected because it was expected that they are the most frequently occurring activities in daily living. The six-minute walk test (6MWT) was included because it represents the fastest participants are likely to walk in their daily lives and because it is a commonly used test for respiratory conditions. Participants were allowed to take breaks between activities, so the total duration of the semi-controlled training portion ranged from 40 to 75 minutes.

TABLE 1

| Activity | Duration | Healthy | | COPD | |
| | | Mean (SD) | Range | Mean (SD) | Range |
| --- | --- | --- | --- | --- | --- |
| 6MWT | 6 min | 20.9 (4.0) | 14-29 | 24.9 (4.5) | 13-34 |
| Sitting | 4 min | 20.6 (5.2) | 10-29 | 17.7 (3.0) | 10-24 |
| Walking | 4 min | 19.7 (4.6) | 13-30 | 25.4 (5.4) | 16-37 |
| Lying | 4 min | 17.6 (2.5) | 14-26 | 15.5 (5.7) | 6-23 |
| Standing | 4 min | 15.2 (5.0) | 4-22 | 18.1 (4.0) | 12-23 |
| Eating | 3 min | 14.9 (2.7) | 9-20 | 17.7 (3.7) | 12-24 |
| Brushing | 2 min | 16.0 (3.7) | 9-25 | 18.5 (4.4) | 11-24 |
| Uncontrolled | 3 hours | 17.4 (4.2) | 6-28 | 19.9 (4.9) | 10-29 |

A second training portion could be considered completely uncontrolled, i.e., collected while a participant conducted an unspecified activity. Participants still wore the smartwatch and chest band, but were free to go about their day outside the lab. After three hours, the participants could take off the smartwatch and chest band. During the data collection, over 53 hours of data from 14 participants was collected, resulting in over 144,800 individual respiratory rate measurements from the chest band. The mean respiratory rate according to the chest band across the entire dataset was 18.31 breaths/min with a standard deviation of 4.72 and a range of 7-29 breaths/min. The range showed the $1^{st}$ and $99^{th}$ percentile of observed values. In TABLE 1, the mean, standard deviation, and range of the respiratory rate is shown by group and activity.

To illustrate the performance of the present embodiments, respiratory rate was also extracted using other approaches, BioWatch and SleepMonitor. BioWatch includes an extractor that first performs noise removal on gyroscope data by applying an averaging filter and then a band-pass Butterworth filter of order two with cut-off frequencies of 4 and 11 Hz. Using this noise-removed data, the BioWatch extractor obtains three respiratory rate predictions by computing an FFT on each of the three axes and selecting the frequency with the highest amplitude between 0.13 Hz and 0.66 Hz (i.e., between 7.8 to 40 breaths/min). To determine which of the three respiratory rate predictions to use, BioWatch examines an FFT amplitude and selects the one from the axis with the greatest amplitude. The BioWatch filter takes the vector magnitude of the derivative of the accelerometer data. Generally, instructions for collecting data from BioWatch require the participants to refrain from movement and stay still. In contrast, using the present embodiments, participants were given very little instruction on how to perform the activities such that they were acting naturally and were not trying to be still. This is evidenced by the fact that for BioWatch, a previous study had the BioWatch filter preserve 85.87% of windows when using a threshold of 0.15, which was the maximum value the BioWatch study observed from their filter during their in-lab study. However, when that same derivative magnitude filter was applied on the present dataset of the example experiments, an average value of 3.56 was observed; if one were to discard windows from the data where the filter value is greater than the original 0.15 threshold, the system would have only accepted 5.14% of windows. This highlights the drastic difference in the amount of motion between data collected out-of-the lab, as in the example experiments, compared to data collected in controlled lab settings, such as for the previous BioWatch study.

The SleepMonitor extractor uses a total variational filter (TV filter) to remove both high and low-frequency noise. After noise removal, respiratory rate estimation is performed on each accelerometer axis using an FFT in a manner similar to BioWatch. However, unlike BioWatch which selects respiratory rate from a single axis, SleepMonitor merges the respiratory rate from all three axes using a Kalman filter. The filter to reject widows looks at the proportion of accelerometer readings in a window with a vector magnitude greater than 10 $m/s^2$. The threshold used in SleepMonitor is 5, so that any window where more than 5% of samples have a vector magnitude greater than 10 $m/s^2$ is rejected For the example experiments, two metrics were considered: accuracy (measured as Mean Absolute Error (MAE)) and frequency (average time between readings). The present embodiments were evaluated on a diverse dataset that includes data from younger, healthy individuals and those with COPD while performing a wide range of activities. Having this diverse dataset allowed the present inventors to analyze how the participant's activity and group affected the performance of the present embodiments. During the example experiments, participants wore a smartwatch and a chest band for ground truth data. In addition to accuracy, the feasibility of running the system 200 in real-time on a smartwatch. Using a combination of data traces and simulation, it was shown that with duty cycling, the system 200 can be run in real-time on a modern smartwatch while providing enough battery life to last a full day.

Figure 6:
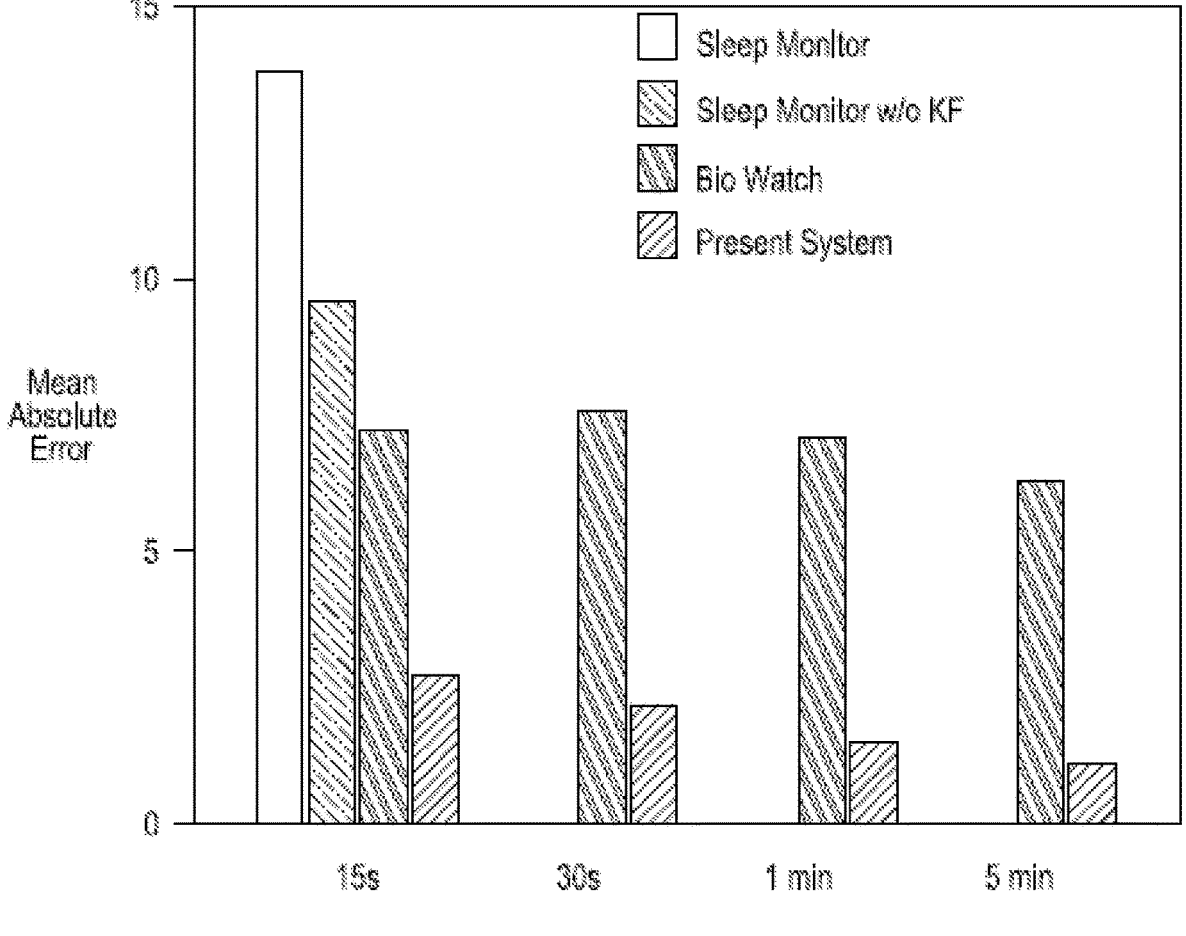
FIG. 6 illustrates compares the error of different threshold values in example experiments for the system of FIG. 1 and for three other approaches.
Figure 7A:
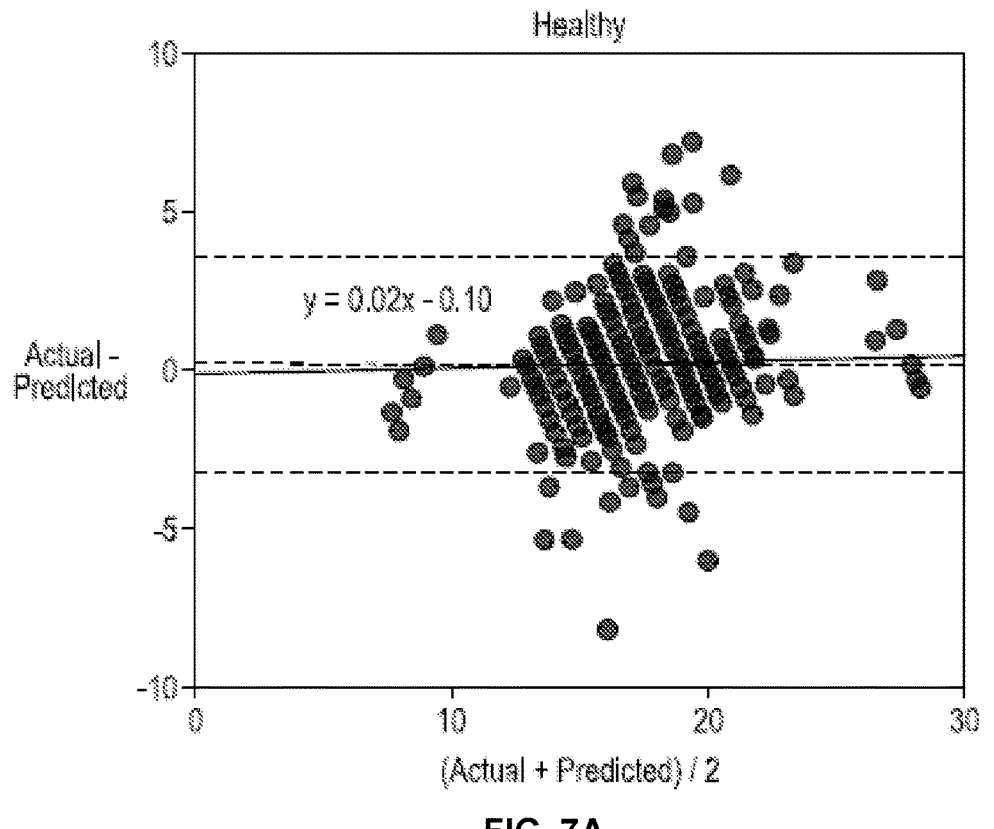
FIG. 7A illustrates a Bland-Altman plot for experimental predictions of a healthy group using the system of FIG. 1.
Figure 7B:
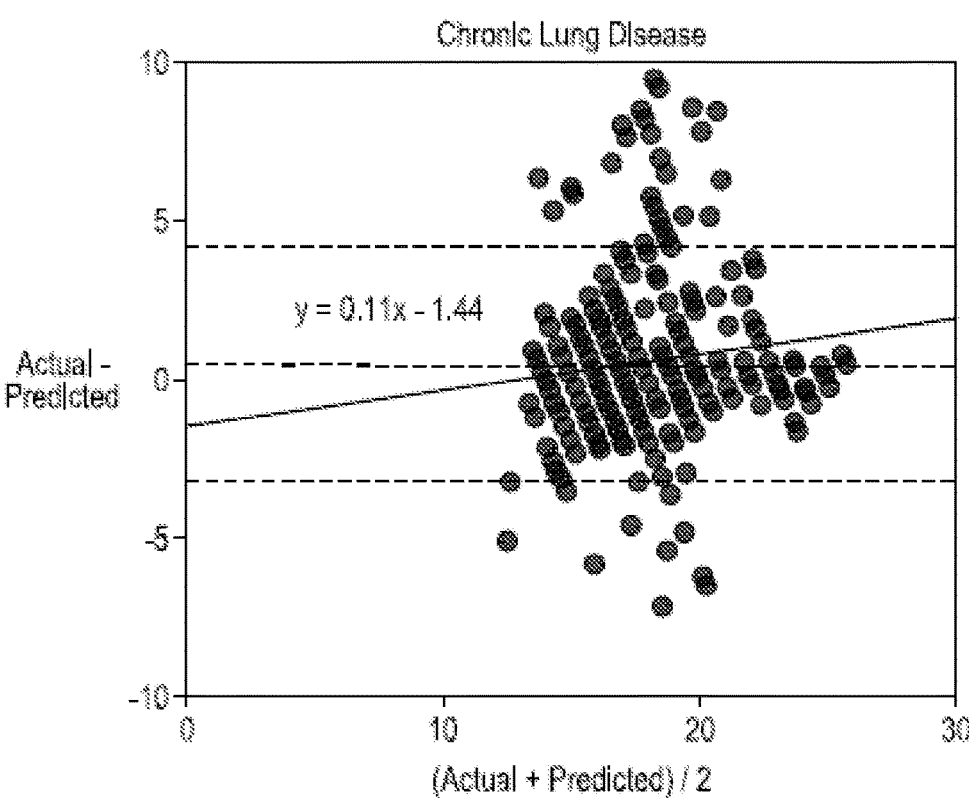
FIG. 7B illustrates a Bland-Altman plot for experimental predictions of a chronic obstructive pulmonary disease (COPD) group using the system of FIG. 1.

In the example experiments, the filter machine learning model uses a random forest filter. With this type of model, using a lower threshold on the random forest filter can increase the accuracy of readings but data is received less frequently. FIG. 6 illustrates different threshold values to produce readings on average every 15 seconds, 30 seconds, 1 minute and 5 minutes. FIG. 6 also shows the mean absolute error at these different frequencies for the present system, BioWatch, SleepMonitor, and SleepMonitor without a Kalman filter (KF). SleepMonitor was only shown for 15 seconds because there was no threshold that resulted in readings at other intervals.

In the example experiments, it was observed that SleepMonitor had a very high error. This may be due to how the Kalman filter used in SleepMonitor relies on exploiting historical readings to boost predictive accuracy. By basing the predicted respiratory rate as a limited change from the posterior/prior respiratory rate in the previous time step, the Kalman filter is able to reduce the random noise caused by sudden movements. This, however, is generally predicated upon the assumption that readings are coming in at consistent time intervals. This assumption does not hold in the wild when a filter is used to discard windows because windows are no longer occurring at consistent time intervals. It was also observed that there was no threshold that could be set that would result in a reading on average every 30 seconds, 1 minute or 5 minutes. For BioWatch, although the frequency at which data is receive could be tuned, there was not an improvement in the MAE as the frequency of readings was decreased.

It was observed that the present embodiments had a significantly lower MAE for all frequencies. When no filter was used, the present embodiments had a MAE of 2.86 compared to BioWatch's 7.01 and SleepMonitor's 9.86, which is a 2.5 and 3.4 times improvement, respectively. When providing a reading every 15 seconds, a 2.6 and 3.5 times improvement was observed (2.73 MAE for the present embodiments, 7.24 for BioWatch and 9.58 for SleepMonitor). At a reading every 5 minutes, the present embodiments had a 5.8 times lower MAE than BioWatch (1.09 vs. 6.30). Advantageously, the present embodiments, in addition to having a substantially lower MAE, also allow tuning of the system to trade frequency for accuracy.

The example experiments highlight advantages of the present embodiments. The extraction machine learning model of the extractor module 292 by itself has a lower MAE than other approaches. Also, despite the extraction machine learning model already having a lower MAE, by applying the filter machine learning model of the filter module 290, the system 200 can further lower the MAE by decreasing reading frequency. Having this trade-off available makes the present embodiments more applicable to a wider range of applications because such applications can decide whether or not the trade-off is worthwhile based on their specific requirements.

In another comparison, the example experiments also controlled the frequency at which the approaches provided readings and compared their accuracy. BioWatch's default threshold value of 0.15, provides a reading on average every 50 seconds with a MAE of 7.49. If a threshold of 1.05 was set with the present embodiments, the same frequency was achieved and a MAE of 2.05 (3.7 times lower). Because SleepMonitor cannot provide a reading on average every 50 seconds, it was not included in the remaining analysis of the present embodiments. Using the thresholds, the MAE and frequency (% of windows accepted) for both the present embodiments and BioWatch were examined during various activities. The results are presented in TABLE 2. Regardless of activity, the present embodiments had a lower MAE than BioWatch. In some cases, BioWatch does accept more windows than the present embodiments. For example, while standing, BioWatch accepts on average 17.2% of windows compared to the present embodiments, which accepts 7.7% of windows. However this increased frequency comes with a much higher MAE (8.2 compared to 1.6). There are also multiple examples of BioWatch not producing any readings during an activity (ex. COPD patients during 6MWT) or only producing readings for one participant (indicated by a missing standard error), but the present embodiments were able to produce readings for multiple participants for all activities examined.

Table 2

TABLE 2 also shows that BioWatch's performance on the COPD group is lower than on healthy participants; illustrating that for other approaches, systems developed on one population may not generalize to other populations. As shown in TABLE 2, using the BioWatch approach, respiratory rate is particularly inaccurate (MAE 12.4) for participants with chronic lung disease when they are lying down. This may be because people with COPD have increased airway obstruction and reduced lung volume while lying down. However, because the filter used by BioWatch summarizes the amount of motion in a window, it accepts quite a few windows while patients are lying down, which leads to large errors. The present embodiments, on the other hand, were trained on participants with chronic lung disease and was able to better learn and recognize their breathing patterns.

To measure agreement between the present embodiments and the ground truth chest band (BioHarness), a Bland-Altman plot was generated. A Bland-Altman plot helps analyze agreement between two measurement methods. For each pair of measurements, it shows the mean of the two against the difference of the two. The Bland-Altman plot for the healthy group and the COPD group is shown in FIGS.

| | BioWatch | | | | Present System | | | |
|---|---|---|---|---|---|---|---|---|
| | Healthy | | COPD | | Healthy | | COPD | |
| Activity | MAE | Freq (%) | MAE | Freq (%) | MAE | Freq (%) | MAE | Freq (%) |
| 6MWT | 7.3 (—) | 4.5 | — (—) | — | 0.8 (0.3) | 10.0 | 0.6 (0.3) | 11.3 |
| Sitting | 5.3 (1.3) | 6.8 | 8.9 (—) | 13.8 | 1.9 (1.5) | 16.5 | 1.2 (0.4) | 10.0 |
| Walking | 7.5 (—) | 27.5 | — (—) | — | 1.6 (0.8) | 20.0 | 0.7 (0.2) | 16.0 |
| Lying | 6.8 (0.8) | 26.7 | 12.4 (2.2) | 30.3 | 1.3 (0.6) | 7.0 | 1.3 (0.7) | 14.8 |
| Standing | 8.2 (3.3) | 17.2 | 7.6 (2.5) | 63.5 | 1.6 (0.7) | 7.7 | 1.3 (0.8) | 12.8 |
| Eating | 3.2 (1.4) | 22.8 | 7.7 (—) | 26.3 | 1.4 (0.5) | 9.2 | 0.6 (0.2) | 17.2 |
| Brushing | 5.7 (4.9) | 8.5 | — (—) | — | 2.1 (1.0) | 5.2 | 1.6 (0.6) | 18.3 |
| Uncontrolled | 6.4 (0.9) | 6.3 | 7.7 (1.2) | 15.7 | 1.5 (0.5) | 4.0 | 2.9 (0.8) | 3.0 |

There can be many reasons why performance is affected by activity. For example, motion makes it harder to isolate the respiratory rate signal. In the examples experiments, high motion activities do not necessarily result in higher error for the present embodiments. The 6MWT, for example, likely had the most motion but one of the lowest errors. This may be because while the amount of motion is high while walking, the participants wrist is moving in a fairly consistent pattern. In this way, random motion may be more detrimental to accuracy than regular, periodic motion. While the respiratory signal is generated by the diaphragm and other muscles in the chest and abdomen, this signal was detected at the wrist. Hence it is likely that the participant's posture and body position affects how well the signal propagates from the abdomen/chest to the wrist. For example, if the participant is lying down, having their watch hand on their chest may produce a much stronger signal than if their hand is by their side. Similarly, the signal quality may be affected by whether the participant is sitting, standing or lying down. These factors would have to be carefully considered with the other approaches. The example experiments illustrates examples of sensor data and respiratory rates obtained from different body positions and the present embodiments were able to learn to extract the signal automatically. In this way, it was demonstrated that the present embodiments were able to produce accurate readings across all activities while other approaches tended to not generate accurate readings during activities involving more motion.

7A and 7B, respectively. For clarity, these graphs only plot a small random sample of data points, however the mean error, limits of agreement and best fit line were computed using all data points. For the healthy group, a fixed bias of 0.19 breaths per minute, proportional bias of 0.02, and limits of agreement between −3.21 and 3.60 were observed. This was a fairly low although significant (one sample t-test p≈0) fixed bias and negligible proportional bias. If desired, the fixed bias can be removed by subtracting 0.19 from the predicted values. The negligible proportional bias suggests that the error in the prediction is not correlated with the magnitude of the predicted value. Finally, the limits of agreement suggest that 95% of the predicted respiratory rates were be within −3.21 and 3.60 of the chest band readings. For the chronic lung disease group, a slightly higher fixed and proportional bias of 0.51 and 0.11, respectively, and limits of agreement between −3.22 and 4.27 were observed. While there was slightly less agreement in the chronic lung disease group than the healthy group, it still showed strong agreement.

While the extraction machine learning model of the filter module 290 was observed to perform excellently in conjunction with the filter machine learning model, in further embodiments, the filter module 290 can also be used with other physiological signal extraction approaches. By training the extraction machine learning model to predict the error of, for example, the BioWatch and SleepMonitor approaches, the present inventors were able to use the filter module 290 to improve the performance of these approaches.

Figure 8A:
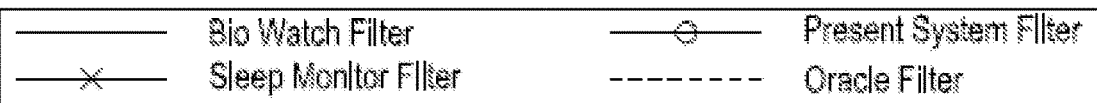
FIG. 8A illustrates experimental results of various filters, including a filter module of the system of FIG. 1, on a BioWatch extractor.
Figure 8A:
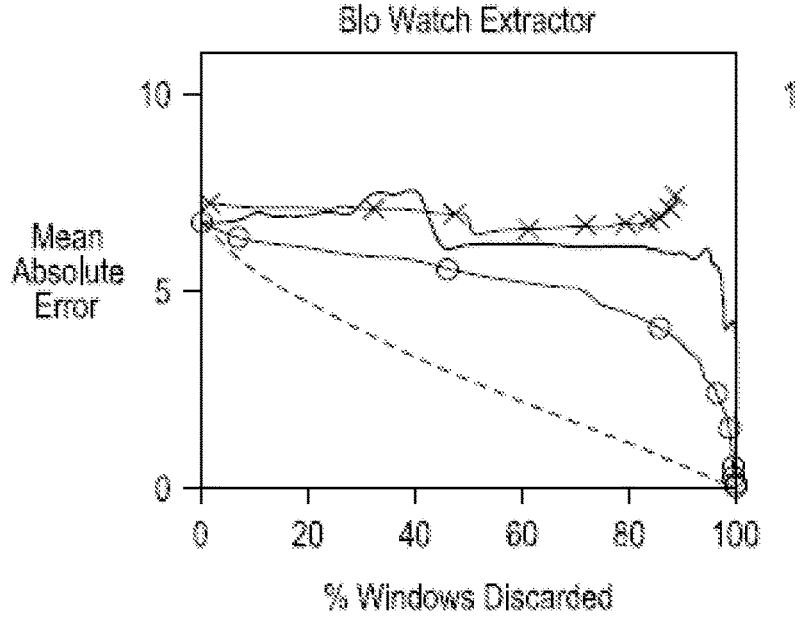
Figure 8B:
FIG. 8B illustrates experimental results of various filters, including the filter module of the system of FIG. 1, on a SleepMonitor extractor.
Figure 8B:
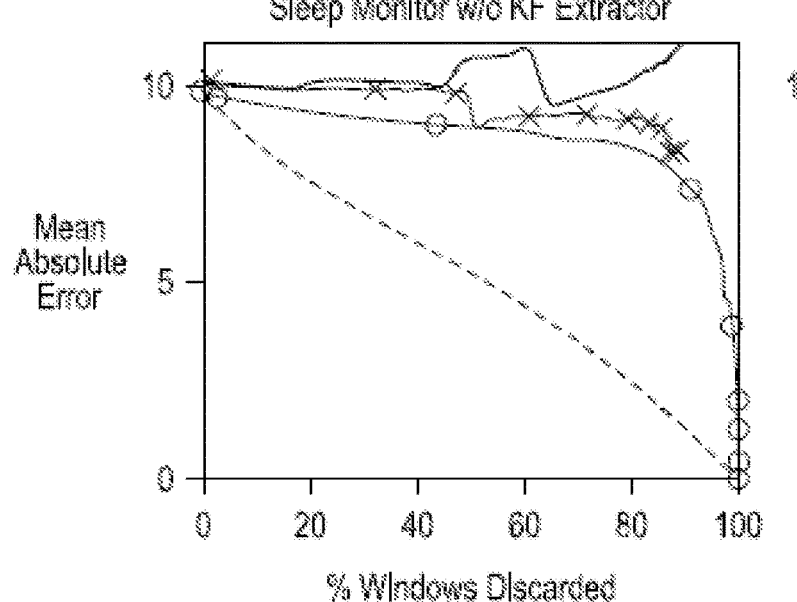
Figure 8C:
FIG. 8C illustrates experimental results of various filters, including the filter module of the system of FIG. 1, on an extractor module of the system of FIG. 1.
Figure 8C:
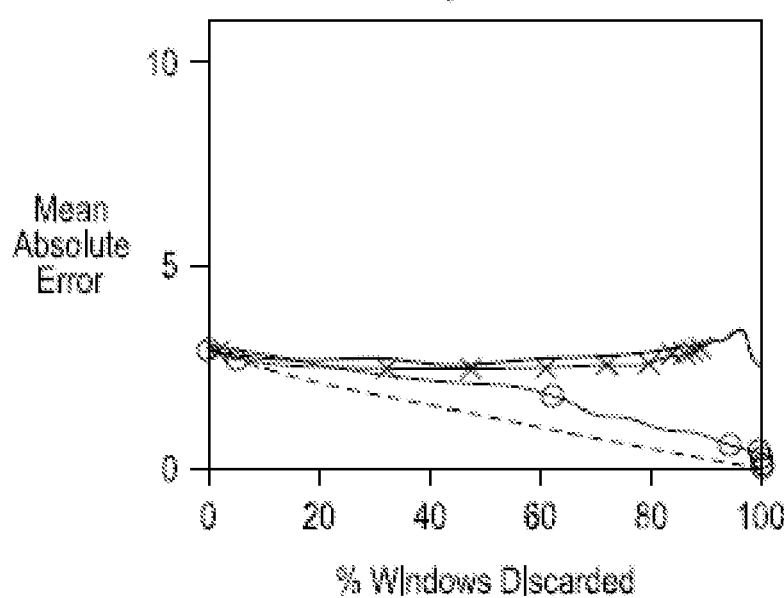

There is a trade-off in selecting a filter threshold. A lower threshold may result in a lower MAE, but generally at the cost of the number of readings. It was observed that with the SleepMonitor filter, even with a threshold of 0, it did not discard 100% of the windows. This is because in each window, there was generally accelerometer readings where there are no forces acting on the smartwatch besides gravity; and therefore the vector magnitude is close to 9.8 m/s². In contrast, the filter module 290 incorporates a useful feature that filters should have, which is that they should allow selecting as much or as little data as desired. It was also observed how the threshold affects the respiratory rate extraction error applying each filter to each extractor. The threshold for each filter was altered and how that affects the number of windows discarded and the mean absolute error when passing the accepted windows to the extractor were observed. The results for this analysis for BioWatch, Sleep-Monitor, and the present system are shown in FIGS. 8A, 8B, and 8C respectively. Simple filters are observed to have not smooth functions, which is not a desirable characteristic for tunability since they make it hard to predict how small changes affect accuracy. The spikes seen in these filters' curves can be attributed to the fact that values these filters are computing were not well-distributed across the threshold domain and there was no direct link between the threshold and filter value. This makes it so that a small change in the filter threshold does not necessarily result in a small change to the number of windows accepted by the filter.

Thus, generally a good filter should be a smooth function that is capable of discarding anywhere from 0% to 100% of the windows. The filter module 290 advantageously meets both these requirements. When used in conjunction with the extractor module 292, it was observed to be much better behaved; in that a small increase to the threshold results in a slight increase in number of windows accepted and MAE. This linear property allows the filter module 290 to be tweaked to the requirements of individual applications. For example, if one wanted to detect respiratory rate with a MAE of 2, they could set the threshold to 1, which would result in a reading roughly every 50 seconds. If one wanted higher accuracy, they could set the threshold to 0.5 which would give a MAE of 1.09 and a reading roughly every 5 minutes. While the observed performance of the filter module 290 also works for the BioWatch and SleepMonitor extractors, performance is not as strong as with the extractor module 292. The filter module 290 has a MAE of 3.48 for the BioWatch extractor and 4.57 for the SleepMonitor extractor.

FIGS. 8A, 8B, and 8C also illustrate the idea of an oracle filter. If the filter's goal is to predict the error in an extractor, the hypothetical oracle is able to do so with 100% accuracy.

Additionally, the oracle knows the extractor's error on all past, present and future windows of data. Therefore, if a threshold of 20 is used with the oracle filter, it only accepts a window if the extractors error on this window is among the lowest 20% of all errors. As seen in FIGS. 8A, 8B, and 8C, none of the filters perform close to the oracle when applied to the BioWatch or SleepMonitor extractors. This is because both the extraction and filter have some error which compounds to make a poorly performing system. However, for the extractor module 292, which has a relatively low error, the performance of the filter module 290 is much closer to the oracle filter. This again suggests that the filter module 290 is learning what makes the extractor module 292 perform substantially well on a window.

Battery life is a critical consideration for any mobile system, such as a smartwatch. In the example experiments, after collecting data from participants and training the Models, the present inventors explored the implication on battery life of running the system 200 on an actual smartwatch. To do so, a combination of actual experiments and simulation were used. The simulation makes use of the IMU data collected from the 14 participants as traces to simulate real-world battery life. Six LG Urbane smartwatches were charged to over 90% battery and the system 200 was run with the screen off until the battery completely drained. Using the initial and final battery level, the mean and standard deviation of change in battery level per hour were determined. The results are shown in TABLE 3:

TABLE 3

| Mode | Battery Δ (%/hour) | |
| --- | --- | --- |
| | Mean | SD |
| Idle | −1.67 | 2.71 |
| Continuous IMU | −5.42 | 0.26 |
| Continuous IMU + RF | −22.52 | 1.47 |
| Continuous IMU + RF + CNN | −22.84 | 1.42 |

Additionally, TABLE 4 shows the simulated battery life of the smartwatch under various recording conditions. To validate the simulator, it was configured to perform on the various modes of operation listed in TABLE 3, for which there was experimental data. Simulating a continuous IMU recording yields an expected 18.5 hours of battery life. This is slightly higher than our experimental observation (approximately 17 hours). The small difference in these battery lives is because in the actual experiments, the devices were charged to anywhere from 90% to 100%, whereas the simulator always begins with 100% battery life.

TABLE 4

| Condition | Actual | | Simulated | |
| --- | --- | --- | --- | --- |
| | Mean | SD | Mean | SD |
| Continuous IMU | 16 h 54 min | 1 h 35 min | 18 h 30 min | 11 min |
| Continuous IMU + run RF | 4 h 17 min | 12 min | 5 h 28 min | 2 min |
| Continuous IMU + run RF and CNN | 3 h 50 min | 26 min | 3 h 57 min | 2 min |
| Present System Continuous | | | 5 h 18 min | 3 min |
| Present System DC (2 min/8 min) | | | 21 h 30 min | 25 min |
| Present System Adaptive DC (n = 3) | | | 1 day 20 h 19 min | 56 min |

In the example experiments, all windows were accepted where the value generated by the filter module 290 is below a predetermined threshold. Because the goal of the filter module 290 is to select windows that will produce a high accuracy reading, accepting all values below a threshold is a way to control for accuracy. If a lower threshold was set, a higher accuracy is desired. While it was empirically found that 90% of readings occur within 90 seconds of each other, there is no guarantee of how long until a reading is produced (although not receiving readings may itself be a useful signal to the system 200). The present embodiments can thus support applications where physiological signals are stochastically received.

Furthermore, while accurate results were achieved using a single threshold value for all participants, further embodiments of the system 200 can further improve accuracy by selecting custom thresholds for each participant/user. However, this would generally require collecting ground truth data from each participant in order to find the desired threshold.

In some embodiments where the system 200 is run on a battery-sensitive device, the filter module 290 could be run in an "always-on, low-power processor" state. When the filter module 290 accepts a window, it can "wake up" the main processor of the device to either run the extractor module 292 on the smartwatch or off-load it to another processor or a cloud-service.

In further embodiments, the method for training the filter module 290 to learn the interaction between the extractor module 292 and a source signal, as described herein, could be applied to other sensing tasks and potentially entirely different domains.

Although the invention has been described with reference to certain specific embodiments, various modifications thereof will be apparent to those skilled in the art without departing from the spirit and scope of the invention as outlined in the claims appended hereto. The entire disclosures of all references recited above are incorporated herein by reference.

The invention claimed is:

1. A computer-implemented method for filtering continuous time-varying data for physiological signal prediction, the method comprising:

receiving the continuous time-varying data from a physical physiological sensor;

segmenting the continuous time-varying data into temporal windows;

using a trained filter machine learning model, predicting an error of predictions of the physiological signal for each temporal window of the time-varying data, the filter machine learning model is trained using physiological signal predictions based on training continuous time-varying data and known values of the physiological signal for the training continuous time-varying data;

discarding, each temporal window of time-varying data when the predicted error for such window is greater than a threshold; and where the temporal window of time-varying data is not discarded, using an extraction machine learning model, determining a physiological signal prediction for each temporal window of the time-varying data, the extraction machine learning model trained using a training set of continuous time-varying data and known values of the physiological signal for the training set of continuous time-varying data, and outputting the physiological signal prediction.

2. The method of claim 1, wherein the threshold is tunable by a user.

3. The method of claim 1, wherein input to the filter machine learning model comprises one or more aggregate measures of the time-varying data.

4. The method of claim 1, wherein the portion of training time-varying data used to train the extraction machine learning model is different than the portion of training time-varying data used to make predictions by the extraction machine learning model for training of the filter machine learning model.

5. The method of claim 4, wherein the portion of training time-varying data used to train the extraction machine learning model comprises uncontrolled data collected while a participant conducted an unspecified activity.

6. The method of claim 1, wherein the physiological signal comprises respiratory rate and the time-varying data comprises continuous motion sensor data from one or more movement sensors.

7. The method of claim 6, wherein the continuous motion sensor data is received from at least one of an accelerometer, a magnetometer and a gyroscope.

8. The method of claim 7, wherein input to the filter machine learning model comprises a plurality of aggregate measures for each axis of the continuous motion sensor data.

9. The method of claim 8, wherein training of the filter machine learning model comprises performing principal component analysis (PCA) on the aggregate measures and passing the PCA output to the filter machine learning model for training.

10. The method of claim 7, wherein an Inertial Measurement Unit (IMU) in a smartwatch comprises at least one of the accelerometer, the magnetometer, and the gyroscope.

11. A system for filtering time-varying data for physiological signal prediction, the continuous time-varying data received from a physical physiological sensor, the system comprising one or more processors and a data storage device, the one or more processors in communication with the data storage device and configured to execute:

an interface module to receive the time-varying data and segment the time-varying data into temporal windows;

a filter module to:

using a trained filter machine learning model, predict an error of predictions of the physiological signal by a trained extraction machine learning model for each temporal window of the time-varying data, the filter machine learning model trained using physiological signal predictions based on training time-varying data and known values of the physiological signal for the training time-varying data;

discard the window of time-varying data when the predicted error for such window is greater than a threshold; and an extractor module to:

where the window of the time varying data is not discarded, use the extraction machine learning model to determine a physiological signal prediction for each temporal window of the time-varying data, the extraction machine learning model trained using a training set of continuous time-varying data and known values of the physiological signal for the training set of continuous time-varying data;

output the physiological signal prediction.

12. The system of claim 11, wherein the threshold is tunable by a user via input to the interface module.

13. The system of claim 11, wherein input to the filter machine learning model comprises one or more aggregate measures of the time-varying data.

14. The system of claim 11, wherein the portion of training time-varying data used to train the extraction machine learning model is different than the portion of training time-varying data used to make predictions by the extraction machine learning model for training of the filter machine learning model.

15. The system of claim 11, wherein the physiological signal comprises respiratory rate and the time-varying data comprises continuous motion sensor data from one or more movement sensors.

16. A computer-implemented method for training two interoperable machine learning models using continuous time-varying training data from a plurality of sources, each source comprising a physical physiological sensor, an extraction machine learning model predicting an outcome on the continuous time-varying data and a filter machine learning model predicting an error of the outcome prediction of the extraction machine learning model, the continuous time-varying training data comprising continuous time-varying data with known outcomes, the method comprising:

training the extraction machine learning model comprising passing a majority portion of the training continuous time-varying data through the extraction machine learning model with the known outcomes as labels for training; and training the filter machine learning model comprising:

passing a minority portion of the training continuous time-varying data through the extraction machine learning model to output predicted outcomes;

determining an error for each predicted outcome compared to the known outcome; and passing the minority portion of the training continuous time-varying data through the filter machine learning model with the determined errors as labels for training.

17. The method of claim 16, wherein the time-varying training data comprises time-varying data from a plurality of sources, and wherein the division of majority portion and minority portion applies to the time-varying training data from each of the plurality of sources.

18. The method of claim 16, wherein a portion of the training time-varying data that is separate from the majority portion and the minority portion is used for testing both the filter machine learning model and the extraction machine learning model.

* * * * *